United States Patent
Miyai et al.

(10) Patent No.: US 9,347,875 B2
(45) Date of Patent: May 24, 2016

(54) GAS ANALYZING SYSTEM

(75) Inventors: Masaru Miyai, Kyoto (JP); Masahiro Nishikawa, Kyoto (JP)

(73) Assignee: HORIBA, LTD., Kyoto, Kyoto (JP)

( * ) Notice: Subject to any disclaimer, the term of this patent is extended or adjusted under 35 U.S.C. 154(b) by 654 days.

(21) Appl. No.: 13/518,693

(22) PCT Filed: Dec. 7, 2010

(86) PCT No.: PCT/JP2010/071865
§ 371 (c)(1),
(2), (4) Date: Jun. 22, 2012

(87) PCT Pub. No.: WO2011/077938
PCT Pub. Date: Jun. 30, 2011

(65) Prior Publication Data
US 2012/0260715 A1    Oct. 18, 2012

(30) Foreign Application Priority Data
Dec. 25, 2009    (JP) ................ 2009-295887

(51) Int. Cl.
*G01N 33/00*    (2006.01)
*G01N 21/3504*    (2014.01)
*G01N 21/27*    (2006.01)

(52) U.S. Cl.
CPC .......... *G01N 21/3504* (2013.01); *G01N 21/274* (2013.01); *G01N 33/0004* (2013.01); *G01N 33/006* (2013.01); *G01N 33/0006* (2013.01)

(58) Field of Classification Search
CPC . G01N 33/006; G01N 1/2273; G01N 1/2252; G01N 33/0037; G01N 33/0039; G01M 15/102
See application file for complete search history.

(56) References Cited

U.S. PATENT DOCUMENTS 4,489,590 A * 12/1984 Hadden .......................... 73/1.04
5,239,492 A *  8/1993 Hartwig et al. ................. 702/27
(Continued)

FOREIGN PATENT DOCUMENTS

CN    1466675 A    1/2004
JP    10300640    11/1998
(Continued)

OTHER PUBLICATIONS

Machine translation of JP 2009-042184, published on Feb. 26, 2009, translation obtained Aug. 29, 2014.*
(Continued)

*Primary Examiner* — David A Rogers
(74) *Attorney, Agent, or Firm* — Brooks Kushman P.C.

(57) ABSTRACT

A gas analyzing system that can perform calibration without being influenced by the deterioration of span gas in a span gas supply line. An open-close device control part that receives a calibration start signal issuing an instruction to start zero calibration and span calibration, and controls an open-close device for a span gas flow path. An open-close device for a zero gas flow path, wherein if the open-close device control part receives a new calibration start signal after a predetermined time has passed since previous calibration was performed, before the span calibration is started, for a predetermined time, the open-close device control part controls the open-close device for the span gas flow path so as to open the open-close device for the span gas flow path, and thereby purges span gas that remains in the span gas flow path.

5 Claims, 3 Drawing Sheets

(56) References Cited

U.S. PATENT DOCUMENTS 5,627,328 A * 5/1997 Sheridan et al. ............ 73/863.83
2004/0055359 A1 * 3/2004 Ketler et al. .................... 73/1.07

FOREIGN PATENT DOCUMENTS

| | | |
|---|---|---|
| JP | 2001013045 | 1/2001 |
| JP | 2001349812 | 12/2001 |
| JP | 2005069874 | 3/2005 |
| JP | 2009042184 | 2/2009 |

OTHER PUBLICATIONS

Shi, Baoshan, Design of the Multi-parameters Gas Detector Based on the AT89S51, China Academic Journal Electronic Publishing House, Jul. 23, 2007, 3 pgs.

International Search Report for PCT/JP2010/071865, English translation attached to original, Both completed by the Japanese Patent Office on Feb. 24, 2011, All together 5 Pages.

* cited by examiner

GAS ANALYZING SYSTEM

CROSS-REFERENCE TO RELATED APPLICATION

This application is the U.S. national phase of PCT Appln. No. PCT/JP2010/071865 filed on Dec. 7, 2010, which claims priority to Patent Application No. 2009-295887 filed on Dec. 25, 2009, the disclosures of which are incorporated in their entirety by reference herein.

TECHNICAL FIELD

The present invention relates to a gas analyzing system that achieves superior measurement accuracy.

BACKGROUND ART

In the past, in the case of measuring concentrations of various types of components in exhaust gas, or various types of components generated or processed in various types of processes, various types of gas analyzers have been used, such as a non-dispersive infrared gas analyzer (NDIR), non-dispersive ultraviolet gas analyzer (NDUV), magnetic oxygen analyzer, chemiluminescence detecting type nitrogen oxide analyzer (CLD type $NO_x$ analyzer), and hydrogen flame ionization detector (FID) (Patent literature 1). In a gas analyzing system provided with such a gas analyzer, before measurement, calibration using zero gas and span gas is performed. In such calibration, first, the zero gas is flowed through the gas analyzer to perform zero calibration, and then the span gas is flowed through the gas analyzer to perform span calibration.

Such zero gas or span gas is generally filled in a high-pressure cylinder, and supplied to the gas analyzing system through a supply line for each gas; however, if calibration has not been performed for a long time, concentration of the span gas remaining in various types of pipes constituting a span gas supply line may be varied, or the gas itself may be denatured or deteriorated.

More specifically, in the case where the span gas supply line is formed of resin pipes such as fluorine resin pipes or nylon pipes, the span gas, or gas in outside air, such as $CO_2$ or $O_2$ may permeate the resin pipes to thereby vary the gas concentration. Also, in the case where the span gas supply line is formed of pipes made of metal, such as stainless steel pipes, some component (e.g., nickel in the case of the stainless steel pipes) contained in the meal may act as a catalyst to denature the span gas.

Even if the calibration is performed with use of the span gas deteriorated as described, appropriate calibration is not performed to cause reductions in accuracy and reliability of an analysis result.

CITATION LIST

Patent Literature

Patent literature 1: JPA 2001-349812

SUMMARY OF INVENTION

Technical Problem

Therefore, the present invention is made to provide a gas analyzing system that can be calibrated without being influenced by such deterioration of the span gas.

Solution to Problem

That is, a gas analyzing system according to the present invention is provided with: a gas analyzer that analyzes a measuring target component contained in sample gas; a span gas flow path that is configured to be able to introduce span gas from a span gas supply source into the gas analyzer, and provided with an open-close device; a zero gas flow path that is configured to be able to introduce zero gas from a zero gas supply source into the gas analyzer, and provided with an open-close device; and an open-close device control part that receives a calibration start signal issuing an instruction to start zero calibration and span calibration, and controls the open-close device for the span gas flow path and the open-close device for the zero gas flow path, wherein if the open-close device control part receives a new calibration start signal after a predetermined time has passed since previous calibration was performed, before the span calibration is started, for a predetermined time, the open-close device control part controls the open-close device for the span gas flow path so as to open the open-close device for the span gas flow path, and thereby purges span gas that remains in the span gas flow path.

If so, in the case of performing the new calibration after the predetermined time has passed since the previous calibration was performed, first, the open-close device for the span gas flow path is opened; span gas remaining in a span gas supply line and the span gas remaining in the span gas flow path are purged to replace the span gas in the span gas supply line and span gas flow path by new one; and then the span calibration can be performed, so that a highly accurate calibration can be performed to obtain a highly reliable analysis result.

Further, the gas analyzing system according to the present invention is provided with a sample gas flow path that is configured to be able to introduce the sample gas from a sample gas supply source into the gas analyzer, and provided with an open-close device, wherein the open-close device control part also controls the open-close device for the sample gas flow path, and preferably, after the span calibration has been finished, controls the open-close device for the sample gas flow path so as to open the open-close device for the sample gas flow path. If so, a series of complicated open-closes of the open-close devices from the calibration to the analysis can be controlled by the single instruction (calibration start signal).

A method for performing span calibration that, in the case of performing new calibration after a predetermined time has passed since previous calibration was performed, first, opens the open-close device for the span gas flow path; purges span gas that remains in the span gas supply line and span gas flow path to replace the span gas in the span gas supply line and span gas flow path by new one; and then performs the span calibration is also one aspect of the present invention. That is, the method for span calibration of a gas analyzing system according to the present invention is a method for performing span calibration of a gas analyzing system that is provided with: a gas analyzer that analyzes a measuring target component contained in sample gas; and a span gas flow path that is configured to be able to introduce span gas from a span gas supply source into the gas analyzer, and provided with an open-close device, the method comprising: if a predetermined time has passed since previous span calibration was performed, opening the open-close device for the span gas flow path; flowing a predetermined amount of the span gas through the span gas flow path to purge span gas that remains in the span gas flow path; and then performing the span calibration.

Advantageous Effects of Invention

As described, according to the present invention, highly accurate calibration can be performed, so that a highly reliable analysis result can be obtained, and even in the case where concentration of a measuring target component in sample gas is low, a highly accurate analysis result can be obtained.

DESCRIPTION OF EMBODIMENTS

In the following, one embodiment of the present invention is described with reference to the drawings.

Figure 1:
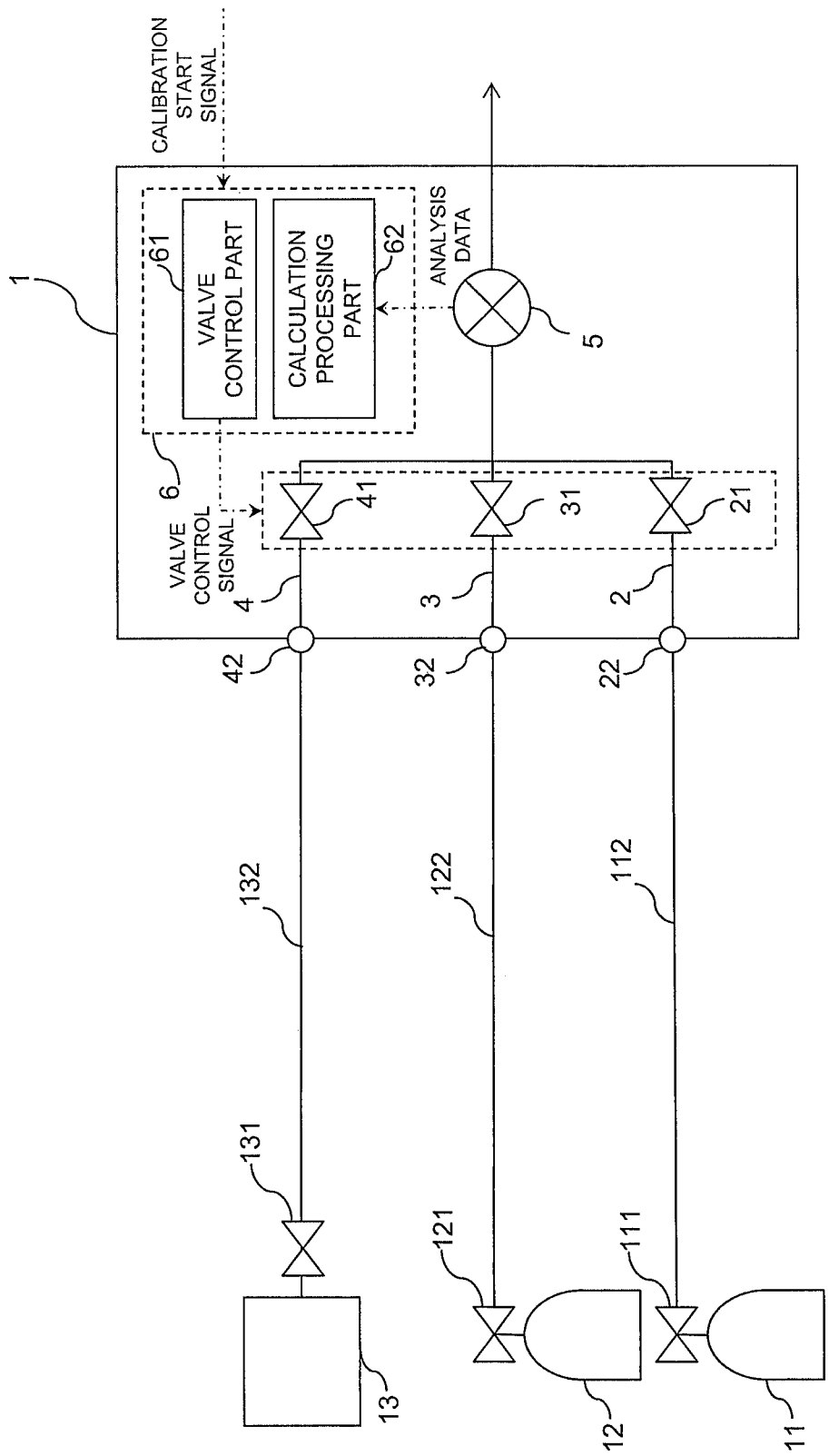
FIG. 1 is a configuration diagram of a gas analyzing system according to one embodiment of the present invention.

A gas analyzing system 1 according to the present embodiment is, as illustrated in FIG. 1, provided with: a zero gas flow path 2; a span gas flow path 3, a sample gas flow path 4, a gas analyzer 5 that is provided on a downstream side of these flow paths and analyzes a measuring target component in sample gas; and an information processor 6.

The zero gas flow path 2, span gas flow path 3, and sample gas flow path 4 are respectively provided with open-close valves 21, 31, and 41, and inlet ports 22, 32, and 42 of the respective flow paths are connected to corresponding gas supply lines 112, 122, and 132. Also, the respective flow paths 2, 3, and 4 are connected to corresponding gas supply sources 11, 12, and 13 through the supply lines 112, 122, and 132.

Each of the gas supply lines 112, 122, and 132 is formed of a resin pipe such as a fluorine resin pipe or nylon pipe, or a metal pipe such as a stainless steel pipe, and has a length of a few 10s to a few 100s m.

As the zero gas supply source 11 and the span gas supply source 12, ones in which corresponding gases are respectively filled in high-pressure cylinders are used, and in both of the high-pressure cylinders, during running of the gas analyzing system 1, their open-close valves 111 and 121 are constantly opened.

As the zero gas, for example, a simulated atmosphere containing 79 vol. % of $N_2$ and 21 vol. % of $O_2$ is used, whereas as the span gas, gas depending on the measuring target component is used, and appropriately selected from, for example, CO, $CO_2$, $NO_x$, $O_2$, $C_3H_8$, $SO_2$, or the like.

As the sample gas supply source 13, for example, any of various types of vehicles, various types of plant facilities, and the like is cited, and the open-close valve 131 provided for the sample gas supply source 13 is also constantly opened during the running of the gas analyzing system 1.

As the gas analyzer 5, one depending on the measuring target component is provided, and for example, in the case where CO and $CO_2$ are to be measured, a non-dispersive infrared gas analyzer (NDIR) is used, in the case where sulfur compounds are to be measured, a non-dispersive ultraviolet gas analyzer (NDUV)) is used, in the case where $O_2$ is to be measured, a magnetic oxygen analyzer is used, in the case where $NO_x$ is to be measured, a chemiluminescence detecting type nitrogen oxide analyzer (CLD type $NO_x$ analyzer) is used, or in the case where THC (hydrocarbon) is to be measured, a hydrogen flame ionization detector (FID) is used.

The information processor 6 is a general-purpose or dedicated one that is provided with, in addition to a CPU, a memory, input means such as a keyboard, output means such as a display, and the like, and configured to store a predetermined program in the memory, and according to the program, cooperatively operate the CPU and its peripheral devices to thereby fulfill functions as a valve control part 61, a calculation processing part 62, and the like.

The valve control part 61 is one that receives a calibration start signal that issues an instruction to start calibration using the zero gas and span gas, and controls the open-close valves 21, 31, and 41 for the zero gas flow path 2, span gas flow path 3, and sample gas flow path 4, respectively, and in the case of receiving a new calibration start signal after a predetermined time has passed since the valve control part 61 received a previous calibration control signal, controls the open-close valve 31 for the span gas flow path 3 and the open-close valve 21 for the zero gas flow path 2 so as to open the open-close valve 31 for the span gas flow path 3 for a predetermined time and then open the open-close valve 21 for the zero gas flow path 2. Note that the calibration start signal specifically refers to input from an operator, a trigger signal from another device, or the like.

The calculation processing part 62 is one that acquires analysis data from the gas analyzer 5, and performs a predetermined calculation process to calculate concentration of the measuring target component.

Figure 2:
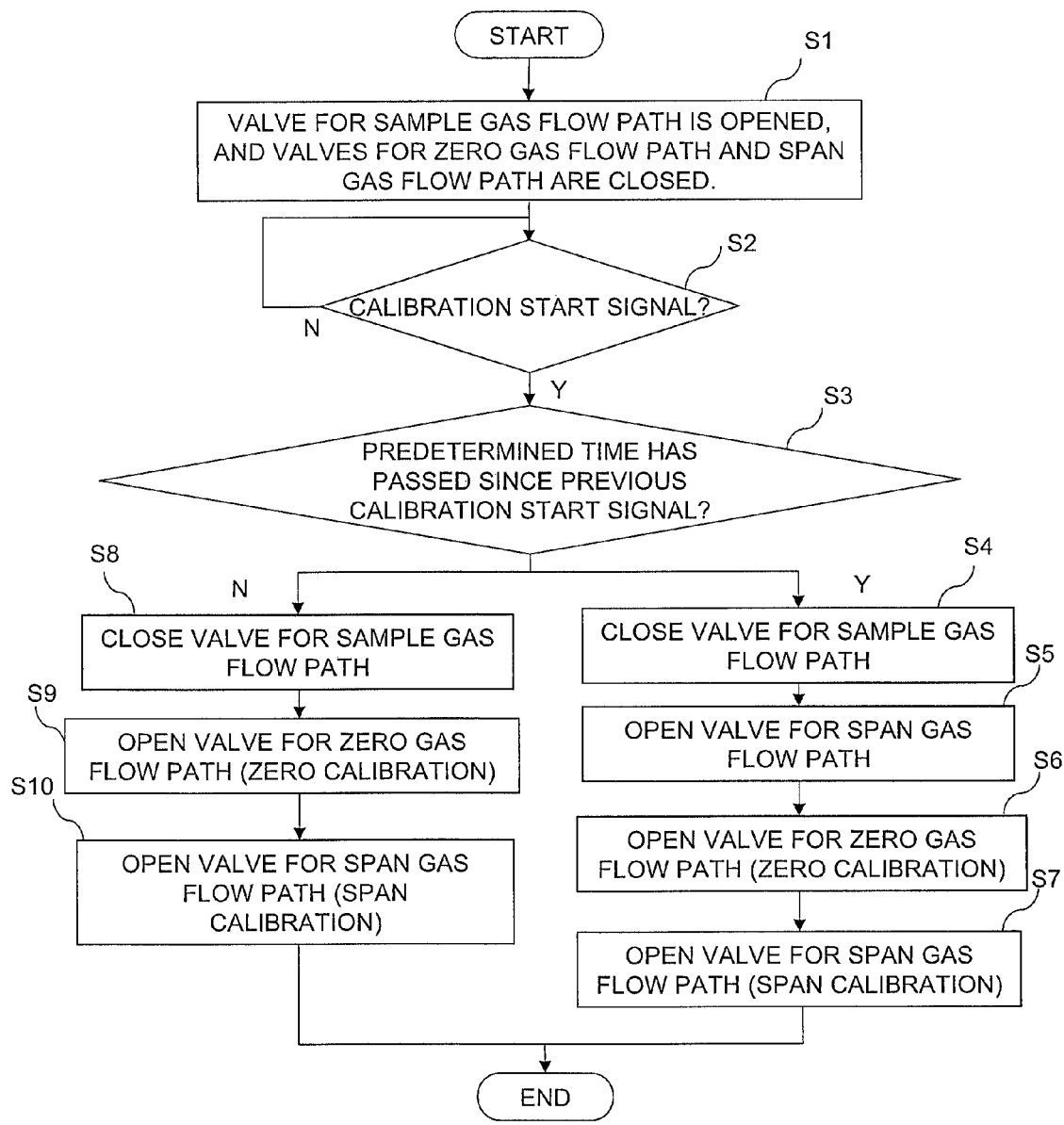
FIG. 2 is a flowchart illustrating a calibration procedure in the same embodiment.

Next, a calibration procedure in the gas analyzing system 1 configured as described is described with reference to a flowchart illustrated in FIG. 2.

First, in a state where the gas analyzing system 1 is analyzing the measuring target component, the open-close valve 41 for the sample gas flow path 4 is opened, whereas the open-close valve 21 for the zero gas flow path 2 and the open-close valve 31 for the span gas flow path 3 are closed (Step S1).

Then, upon receipt of the calibration start signal such as input from an operator, a trigger signal from another device, or the like (Step S2), the valve control part 61 determines whether or not a predetermined time A has passed since the valve control part 61 received a previous calibration signal (Step S3).

Here, the predetermined time A is a constant time that is preliminarily set on the basis of a material for the pipe constituting the span gas supply line 122, a length of the pipe, the type of the span gas, and the like, and for example, in the case where the span gas supply line 122 is formed of a fluorine resin pipe, approximately 90 minutes to 2 hours. In addition, the predetermined time A can be changed after having been set once.

If the predetermined time A has passed, the valve control part 61 controls the respective open-close valves 21, 31, and 41 as follows. That is, first, the valve control part 61 closes the open-close valve 41 for the sample gas flow path 4 (Step S4). Then, the valve control part 61 opens the open-close valve 31 for the span gas flow path 3 for a predetermined time B to purge span gas remaining in the span gas supply line 122 and span gas flow path 3 to the outside of the gas analyzing system 1, and replaces the span gas in the span gas supply line 122 and span gas flow path 3 by new one (Step S5). In addition, the predetermined time B is a constant time that is preliminarily set according to lengths of the span gas supply line 122 and span gas flow path 3, a flow rate (pressure) of the span gas, and the like.

Then, after the predetermined time B has passed, the valve control part 61 closes the open-close valve 31 for the span gas flow path 3; then opens the open-close valve 21 for the zero gas flow path 2 to perform zero calibration (Step S6); after the zero calibration has been finished, closes the open-close valve 21 for the zero gas flow path 2; and continuously opens the open-close valve 31 for the span gas flow path 3 to perform span calibration (Step S7).

On the other hand, if the predetermined time A has not passed, the valve control part 61 controls the respective open-close valves 21, 31, and 41 as follows. That is, the valve control part 61 closes the open-close valve 41 for the sample gas flow path 4 (Step S8); then immediately opens the open-close valve 21 for the zero gas flow path 2 to perform zero calibration (Step S9); after the zero calibration has been finished, closes the open-close valve 21 for the zero gas flow path 2; and continuously opens the open-close valve 31 for the span gas flow path 3 to perform span calibration (Step S10).

Then, in either case, after the span calibration has been finished, the valve control part 61 closes the open-close valve 31 for the span gas flow path 3, and then opens the open-close valve 41 for the sample gas flow path 4 to start to analyze the measuring target component contained in the sample gas.

Figure 3:
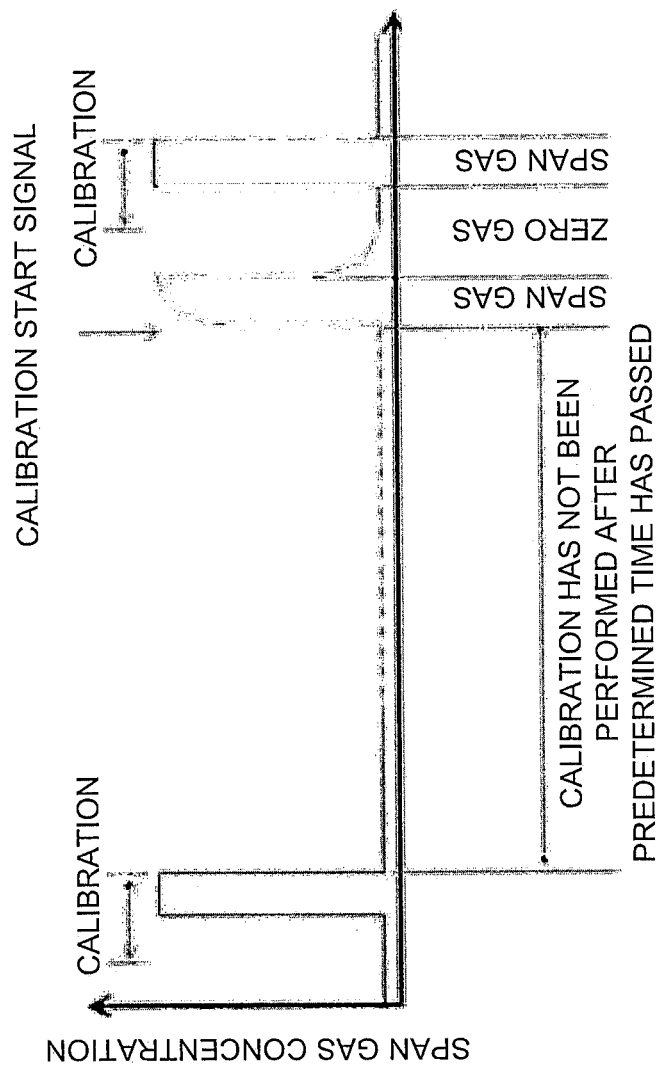
FIG. 3 is a graph illustrating concentration of span gas in the same embodiment.

As a result of performing the new calibration as described above after the predetermined time has passed since the previous calibration and then measuring concentration of the span gas, a graph as illustrated in FIG. 3 is obtained. As illustrated in the graph, the span gas remaining in the span gas supply line 122 for the predetermined time is deteriorated, and therefore even if the span gas is directly used to perform the span calibration, adequate calibration cannot be performed. Note that in an aspect illustrated in FIG. 3, the sample gas has not been analyzed after the previous calibration. Also, the zero calibration is performed after the constant time has passed since the valve control part 61 opened the open-close valve 21 for the zero gas flow path 2 to start to flow the zero gas, and consequently the span gas has been sufficiently purged to the outside of the gas analyzing system 1.

According to the gas analyzing system 1 configured as described according to the present embodiment, in the case where a new calibration start signal is received after the predetermined time has passed since a previous calibration start signal was received, first, the open-close valve 31 for the span gas flow path 3 is opened for the predetermined time or more to purge span gas remaining in the span gas supply line 122 and span gas flow path 3, and then the span gas in the span gas supply line 122 and span gas flow path 3 is replaced by new one to perform the calibration. For this reason, highly accurate calibration can be performed to obtain a highly reliable analysis result.

Note that the present invention is not limited to the above-described embodiment.

For example, the gas analyzing system according to the present invention may be provided with a plurality of types of gas analyzers.

The present invention may be configured such that the function of the calculation processing part in the above-described embodiment is carried by an external information processor.

In the above-described embodiment, the remaining span gas is also purged to the outside of the system through the gas analyzer; however, a branch path for purging the remaining span gas to the outside of the system may be separately provided.

Besides, it should be appreciated that the above-described embodiment and variations may be partially or wholly appropriately combined, and without departing from the scope of the present invention, various modifications can be made.

INDUSTRIAL APPLICABILITY

According to the present invention, by performing highly accurate calibration, a highly reliable analysis result can be obtained, and even in the case where concentration of a measuring target component in sample gas is low, a highly accurate analysis result can be obtained.

REFERENCE SIGNS LIST

1: Gas analyzing system
2: Zero gas flow path
21: Open-close valve for zero gas flow path (open-close device)
3: Span gas flow path
31: Open-close valve for span gas flow path (open-close device)
5: Gas analyzer
61: Valve control part (open-close device control part)

The invention claimed is:
1. An exhaust gas analyzing system comprising:
a gas analyzer that analyzes a measuring target component contained in sample gas;
a span gas flow path that is configured to be able to introduce span gas from a span gas supply source into the gas analyzer, and provided with an open-close device;
a span gas supply line that connects the span gas supply source and the span gas flow path;
a zero gas flow path that is configured to be able to introduce zero gas from a zero gas supply source into the gas analyzer, and provided with an open-close device;
an open-close device control part that receives a calibration start signal issuing an instruction to start zero calibration and span calibration, and controls the open-close device for the span gas flow path and the open-close device for the zero gas flow path, and
an information processor unit having a CPU, a memory, and a valve control signal output cooperating with the open-close device control part, the information processor unit storing a program operated on the CPU wherein;
if the open-close device control part receives a new calibration start signal after a predetermined time A, that is a predicted time that the span gas deteriorates, has passed since previous calibration was performed, before the span calibration is started, the open-close device control part controls the open-close device for the span gas flow path so as to open the open-close device for the span gas flow path for a predetermined time B, and thereby replaces the deteriorated span gas that remains in the span gas supply line and the span gas flow path, where the predetermined time B is set to be able to replace all of remaining deteriorated span gas in the span gas supply line and the span gas flow path with new span gas wherein,
if the open-close device control part receives the new calibration start signal after the predetermined time A has passed since previous calibration was performed, the open-close device control part opens the open-close device for the span gas flow path for the predetermined time B,
after replacing the remaining deteriorated span gas the open-close device control part closes the open-close device for the span gas flow path; and continuously opens the open-close device for the zero gas flow path, and after the zero calibration by introducing the zero gas from the zero gas supply source has been finished, the open-close device control part closes the open-close device for the zero gas flow path and continuously opens the open-close device for the span gas flow path in order to start the span calibration by introducing the span gas from the span gas supply source.

2. The exhaust gas analyzing system according to claim 1, comprising a sample gas flow path that is configured to be able to introduce the sample gas from a sample gas supply source into the gas analyzer, and provided with an open-close device, wherein the open-close device control part also controls the open-close device for the sample gas flow path, and after the span calibration has been finished, controls the open-close device for the sample gas flow path so as to open the open-close device for the sample gas flow path.

3. The gas analyzing system according to claim 1, wherein the open-close device control part closes the open-close device for span gas flow path after the predetermined time B has passed, then opens the open-close device for the zero gas flow path, after the zero calibration has been finished, the open-close device control part closes the open-close device for the zero gas flow path; and continuously opens the open-close device for the span gas flow path.

4. A method for performing span calibration of an exhaust gas analyzing system that comprises: a gas analyzer that analyzes a measuring target component contained in sample gas; and a span gas flow path that is configured to be able to introduce span gas from a span gas supply source into the gas analyzer, a span gas supply line that connects the span gas supply source and the span gas flow path, and provided with an open-close device, the method comprising:

if a predetermined time A, that is a predicted time that the span gas deteriorates, has passed since previous span calibration was performed, opening the open-close device for the span gas flow path;

flowing a predetermined amount of the span gas through the span gas supply source and the span gas flow path to replace all of the span gas that remains in the span gas supply source and the span gas flow path; and then performing the span calibration, wherein the predetermined amount is set to be able to replace all of remaining deteriorated span gas in the span gas supply line and the span gas flow path with new span gas.

5. An exhaust gas analyzing system comprising:

a gas analyzer that analyzes a measuring target component contained in sample gas;

a span gas flow path that is configured to be able to introduce span gas from a span gas supply source into the gas analyzer, and provided with an open-close device;

a span gas supply line that connects the span gas supply source and the span gas flow path;

a zero gas flow path that is configured to be able to introduce zero gas from a zero gas supply source into the gas analyzer, and provided with an open-close device; and an open-close device control part that receives a calibration start signal issuing an instruction to start zero calibration and span calibration, and controls the open-close device for the span gas flow path and the open-close device for the zero gas flow path, and an information processor unit having a CPU, a memory, and a valve control signal output cooperating with the open-close device control part, the information processor unit storing a program operated on the CPU wherein:

if the open-close device control part receives a new calibration start signal after a predetermined time A, that is a predicted time that the span gas deteriorates, has passed since previous calibration was performed, before the span calibration is started, the open-close device control part controls the open-close device for the span gas flow path so as to open the open-close device for the span gas flow path while a predetermined time B, and thereby replaces span gas that remains in the span gas flow path, the predetermined time B is set to be able to replace all of remaining deteriorated span gas in the span gas supply line and the span gas flow path with new span gas, wherein if the open-close device control part receives the new calibration start signal before the predetermined time A has passed since previous calibration was performed, the open-close device control part opens the open-close device for the zero gas flow path without purging the span gas, and after the zero calibration has been finished, the open-close device control part closes the open-close device for the zero gas flow path, then opens the open-close device for the span gas flow path.

* * * * *